(12) United States Patent
Dubeau et al.

(10) Patent No.: US 11,730,513 B2
(45) Date of Patent: Aug. 22, 2023

(54) SUBCUTANEOUS IMPLANT INTEGRATED INSTRUMENT WITH POCKET CREATOR

(71) Applicant: Cardiac Pacemakers, Inc., St. Paul, MN (US)

(72) Inventors: Serge Dubeau, Plymouth, MN (US); Tyler Thompson, St. Michael, MN (US); Kathryn Sick, Shoreview, MN (US)

(73) Assignee: Cardiac Pacemakers, Inc., St Paul, MN (US)

( * ) Notice: Subject to any disclaimer, the term of this patent is extended or adjusted under 35 U.S.C. 154(b) by 343 days.

(21) Appl. No.: 16/983,653

(22) Filed: Aug. 3, 2020

(65) Prior Publication Data

US 2020/0360052 A1 Nov. 19, 2020

Related U.S. Application Data

(63) Continuation of application No. 15/486,268, filed on Apr. 12, 2017, now Pat. No. 10,729,463.

(60) Provisional application No. 62/322,236, filed on Apr. 13, 2016.

(51) Int. Cl.
    *A61B 17/34* (2006.01)
    *A61N 1/372* (2006.01)
    *A61M 37/00* (2006.01)

(52) U.S. Cl.
    CPC .......... *A61B 17/3468* (2013.01); *A61N 1/372* (2013.01); *A61B 2017/347* (2013.01); *A61B 2560/063* (2013.01); *A61M 37/0069* (2013.01)

(58) Field of Classification Search
    CPC .......... A61B 17/3468; A61B 2017/347; A61B 2560/063; A61M 37/0069
    See application file for complete search history.

(56) References Cited

U.S. PATENT DOCUMENTS

| | | | |
|---|---|---|---|
| 4,077,406 A * | 3/1978 | Sandhage | A61M 37/0069 604/61 |
| 5,304,119 A | 4/1994 | Balaban et al. | |
| 5,405,324 A | 4/1995 | Wiegerinck | |
| 6,939,318 B2 | 9/2005 | Stenzel | |
| 7,736,330 B2 | 6/2010 | Bardy | |

(Continued)

FOREIGN PATENT DOCUMENTS

| | | |
|---|---|---|
| CN | 105142551 A | 12/2015 |
| WO | 2017035038 A1 | 3/2017 |

OTHER PUBLICATIONS

International Search Report and Written Opinion issued in PCT/US2017/027278, dated Jul. 7, 2017, 10 pages.

(Continued)

*Primary Examiner* — Tuan V Nguyen
(74) *Attorney, Agent, or Firm* — Faegre Drinker Biddle & Reath LLP (57) ABSTRACT

Aspects of the present disclosure are directed toward apparatuses, methods, and systems comprising an introducer for facilitating subcutaneous implantation of a medical device. The introducer includes a housing, a tunneler extending from the housing, an inserter configured to move along a pathway to pass the medical device through the housing, a compartment configured to releasably hold and contain the medical device prior to the inserter moving the medical device, and a snap-feature integrally formed by the housing.

18 Claims, 6 Drawing Sheets

(56) References Cited

U.S. PATENT DOCUMENTS

| | | | |
|---|---|---|---|
| 10,052,489 B2 | 8/2018 | Katra et al. | |
| 10,548,632 B2 | 2/2020 | Sick et al. | |
| 2002/0188247 A1* | 12/2002 | Peery | A61M 37/0069 600/7 |
| 2003/0208153 A1 | 11/2003 | Stenzel | |
| 2006/0258974 A1* | 11/2006 | Kennedy | A61M 25/01 604/22 |
| 2010/0331868 A1 | 12/2010 | Bardy | |
| 2011/0184449 A1 | 7/2011 | Lubock et al. | |
| 2011/0270264 A1 | 11/2011 | Shoji et al. | |
| 2013/0313133 A1* | 11/2013 | Walters | A61M 37/0069 600/309 |
| 2014/0276928 A1 | 9/2014 | Vanderpool et al. | |
| 2016/0175007 A1 | 6/2016 | Valbuena et al. | |
| 2016/0279397 A1 | 9/2016 | Katra et al. | |
| 2016/0331398 A1 | 11/2016 | Foster et al. | |
| 2017/0296229 A1 | 10/2017 | Sick et al. | |
| 2017/0296230 A1 | 10/2017 | Dubeau et al. | |
| 2020/0163698 A1 | 5/2020 | Cornelius et al. | |

OTHER PUBLICATIONS

International Search Report and Written Opinion issued in PCT/US2017/027279, dated May 19, 2017, 14 pages.
Extended European Search Report for EP 22159617.4, dated Jun. 22, 2022.

* cited by examiner

Fig. 2C

SUBCUTANEOUS IMPLANT INTEGRATED INSTRUMENT WITH POCKET CREATOR

CROSS-REFERENCE TO RELATED APPLICATION

This application is a continuation application off of U.S. application Ser. No. 15/486,268, file Apr. 12, 2017, which claims priority to Provisional Application No. 62/322,236, filed Apr. 13, 2016, which is herein incorporated by reference in its entirety.

TECHNICAL FIELD

The present disclosure relates to medical devices and methods for creating a pocket in a patient for an implantable medical device. More specifically, the disclosure relates to devices and methods for facilitating implantation of the implantable medical device under the patient's skin.

BACKGROUND

Medical devices may be implanted subcutaneously under a patient's skin with relatively little intervention and without deeply positioning the device in the patient's body. Positioning of the medical device may be difficult due to high insertion forces necessary to manipulate the medical device and form a pocket for the device under the patient's skin. Improperly positioning functional aspects of the device may result in poor performance. This may include forming a pocket that is too large for the medical device, or forming a pocket having improper dimensions. In addition, improper pocket formation may result in difficult placement of the implantable medical device during the operation and/or the implantable medical device being ejected prior to sealing the pocket (e.g., stitching the incision). Further, improper pocket formation may result in an implanted device being ejected from a patient as a result of the patient's normal movement. Thus, there is a need for an introducer device that allows for improved pocket formation and positioning of an implantable medical device within the pocket.

SUMMARY

In Example 1, an introducer apparatus for facilitating subcutaneous implantation of a medical device, the apparatus comprising: a housing having a proximal end and a distal end, the housing defining a distal opening at or adjacent to the distal end; and an inserter configured to form a subcutaneous pocket in tissue of a patient and to move the medical device through the distal opening of the housing, the inserter having a first portion configured to facilitate forming the subcutaneous pocket, and a second portion configured to facilitate moving the medical device through the distal opening of the housing, and, the first portion being configured to disengage from the second portion.

In Example 2, the apparatus of Example 1, wherein the housing comprises a proximal opening and a first channel between the proximal opening and the distal opening along a length of the housing, and each of the first portion and the second portion are configured to move within the first channel along the length of the housing, and wherein the inserter configured to form the subcutaneous pocket without rotation of the housing or the inserter.

In Example 3, the apparatus of any of Examples 1-2, wherein the first portion comprises a proximal end and a distal end, a first handle portion arranged at the proximal end of the first portion, and a first extension portion extending from the first handle portion.

In Example 4, the apparatus of Example 3, wherein the second portion comprises a proximal end and a distal end, a second handle portion arranged at the proximal end of the second portion, a second extension portion extending from the second handle portion, and the second portion comprises a second channel along a length of the second extension portion.

In Example 5, the apparatus of Example 4, wherein the first portion is configured to move within the second channel.

In Example 6, the apparatus of Example 5, wherein the first handle portion comprises a first upper surface and a first lower surface, the second handle portion comprises a second upper surface and a second lower surface, and the first lower surface and the second upper surface are corresponding surfaces.

In Example 7, the apparatus of Example 6, wherein the first handle portion is configured to nest within the second handle portion.

In Example 8, the apparatus of Example 4, wherein the first extension portion has a first length, and the second extension portion has a second length, and the first length is greater than the second length.

In Example 9, the apparatus of Example 8, wherein each of the first extension portion and the second extension portion are configured to extend through the distal opening of the housing in a fully-extended configuration of the first portion and the second portion.

In Example 10, the apparatus of Example 9, wherein the second extension portion is configured to extend through the distal opening of the housing in a fully-extended configuration of the second portion after the first portion is disengaged from the second portion.

In Example 11, the apparatus of any of Examples 1-10, wherein the second portion includes lateral extensions configured to prevent the second portion from disengaging from the housing.

In Example 12, the apparatus of any of Examples 1-11, further including a removable lock structure configured to hold the first portion and the second portion relative to the housing in an initial configuration.

In Example 13, the apparatus of Example 12, wherein the housing includes a proximal opening and a first channel between the proximal opening and the distal opening along a length of the housing, and each of the first portion and the second portion are configured to move within the first channel along the length of the housing after removal of the removable lock structure.

In Example 14, the apparatus of any of Examples 2-13, wherein the housing comprises a compartment laterally adjacent to the first channel, wherein the compartment is configured to releasably hold and contain the medical device.

In Example 15, the apparatus of any of Examples 1-14, wherein the inserter is configured to form the subcutaneous pocket without rotation of the housing or the inserter.

In Example 16, a housing having a proximal end and a distal end, the housing defining a distal opening at or near the distal end; a tunneler configured to facilitate forming a subcutaneous pocket for the medical device and extend from the distal end of the housing; and an inserter configured to form the subcutaneous pocket in tissue of a patient and to move the medical device through the distal opening of the housing, the inserter having a first portion configured to facilitate forming the subcutaneous pocket, and a second portion configured to facilitate moving the medical device through the distal opening of the housing, and, the first portion being configured to disengage from the second portion.

In Example 17, the apparatus of Example 16, wherein the inserter is configured to form the subcutaneous pocket without rotation of the housing or the inserter.

In Example 18, the apparatus of Example 16, wherein the first portion of the inserter comprises a proximal end and a distal end, and a first handle portion arranged at the proximal end of the first portion.

In Example 19, the apparatus of Example 17, wherein the second portion comprises a proximal end and a distal end, and a second handle portion arranged at the proximal end of the second portion.

In Example 20, the apparatus of Example 18, wherein the first handle portion comprises a first upper surface and a first lower surface, the second handle portion comprises a second upper surface and a second lower surface, and the first lower surface and the second upper surface are corresponding surfaces.

In Example 21, the apparatus of Example 19, wherein the first handle portion is configured to nest within the second handle portion.

In Example 22, the apparatus of Example 16, wherein the housing comprises a proximal opening and a first channel between the proximal opening and the distal opening along a length of the housing, and each of the first portion and the second portion are configured to move within the first channel along the length of the housing.

In Example 23, the apparatus of Example 22, wherein the second portion comprises a second channel along a length thereof, and wherein the first portion is configured to move within the second channel.

In Example 24, the apparatus of Example 16, wherein the first portion of the inserter comprises a proximal end and a distal end, a first handle portion arranged at the proximal end of the first portion, and a first extension portion extending from the first handle portion.

In Example 25, the apparatus of Example 24, wherein the second portion comprises a proximal end and a distal end, and a second handle portion arranged at the proximal end of the second portion, and a second extension portion extending from the second handle portion.

In Example 26, the apparatus of Example 25, wherein the first extension portion has a first length, and the second extension portion has a second length, and the first length is greater than the second length.

In Example 27, the apparatus of Example 26, wherein each of the first extension portion and the second extension portion are configured to extend through the distal opening of the housing in a fully-extended configuration of the first portion and the second portion.

In Example 28, the apparatus of Example 27, wherein the second extension portion is configured to extend through the distal opening of the housing in a fully-extended configuration of the second portion after the first portion is disengaged from the second portion.

In Example 29, a system comprising: a medical device; and an introducer apparatus for facilitating subcutaneous implantation of the medical device, the apparatus comprising: a housing having a proximal end and a distal end, the housing defining a distal opening at or adjacent to the distal end, a tunneler configured to facilitate forming a subcutaneous pocket for the medical device and extend from the distal end of the housing, and an inserter configured to form a subcutaneous pocket in tissue of a patient and to move the medical device through the distal opening of the housing, the inserter having a first portion configured to facilitate forming the subcutaneous pocket, and a second portion configured to facilitate moving the medical device through the distal opening of the housing, and, the first portion being configured to disengage from the second portion.

In Example 30, the system of Example 29, wherein the inserter further comprises a first portion having a first handle portion and a second portion having a second handle portion, wherein the first handle portion is configured to nest within the second handle portion.

In Example 31, the system of Example 29, wherein the second portion comprises lateral extensions configured to prevent the second portion from disengaging from the housing.

In Example 32, a method of subcutaneous implanting a medical device using an introducer apparatus comprising a housing having a proximal end, a distal end, and a distal opening defined by the housing, and a tunneler extending from the housing, and an inserter having a first portion and a second portion, the method comprising: making an incision in a patient's skin; positioning the introducer apparatus within the incision using the tunneler; forming a subcutaneous pocket for the medical device using the first portion of the inserter; removing the first portion of the inserter from the second portion of the inserter; and ejecting the medical device into the subcutaneous pocket through the distal opening of the housing using the second portion of the inserter.

In Example 33, the method of Example 32, wherein forming the subcutaneous pocket includes using the first portion of the inserter to force apart tissue under the patient's skin without rotation of the housing or the inserter.

In Example 34, the method of Example 33, further comprising moving the second portion of the inserter distally relative to the housing prior to ejecting the medical device through the distal opening of the housing via the second portion.

In Example 35, the method of Example 34, further comprising loading the medical device into a compartment in the housing prior to positioning the introducer apparatus within the incision using the tunneler.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

While the disclosed subject matter is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

As the terms are used herein with respect to ranges of measurements (such as those disclosed immediately above), "about" and "approximately" may be used, interchangeably, to refer to a measurement, position, or arrangement, that includes the stated measurement, position, or arrangement and that also includes any measurement, positions, or arrangements that are reasonably close to the stated measurement, position, or arrangement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, positions, or arrangements, adjustments made to optimize performance and/or structural parameters in view of differences in measurements, positions, or arrangements associated with other components, particular implementation scenarios, imprecise adjustment and/or manipulation of objects by a person or machine, and/or the like.

Although the term "block" may be used herein to connote different elements illustratively employed, the term should not be interpreted as implying any requirement of, or particular order among or between, various steps disclosed herein unless and except when explicitly referring to the order of individual steps. Additionally, a "set" or "group" of items (e.g., inputs, algorithms, data values, etc.) may include one or more items, and, similarly, a subset or subgroup of items may include one or more items.

DETAILED DESCRIPTION

Figure 1:
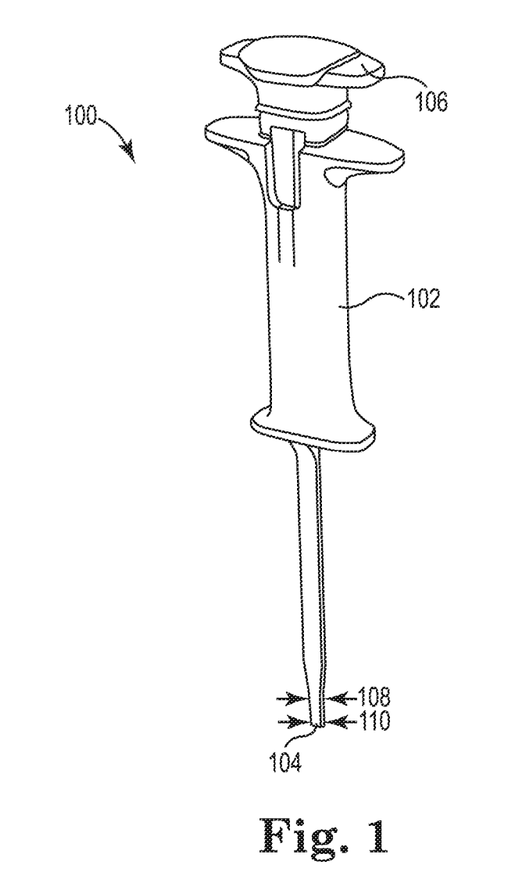
FIG. 1 is a perspective view of an illustrative introducer apparatus for a medical device, in accordance with embodiments of the disclosure.

FIG. 1 is a perspective view of an illustrative introducer apparatus 100 for a medical device (not shown), in accordance with embodiments of the disclosure. The introducer apparatus 100 includes a housing 102. The housing 102 may include a compartment or internal area (as discussed in further detail below, for example, with reference to FIGS. 2A-2C) that is configured to releasably hold the medical device. The housing 102, the compartment or internal area, is configured to hold the medical device, and may be formed or manufactured to accommodate medical devices of various sizes.

As also shown in FIG. 1, the introducer apparatus 100 also may also include an inserter 106. The inserter 106 may be configured to extend through a distal opening defined by the housing (as discussed in further detail below, for example, with reference to FIGS. 2A-2C and FIGS. 3A-F). In addition, the inserter 106 may be configured to form a subcutaneous pocket in tissue of a patient and move the medical device through the distal opening (from within the housing 102).

Further, the introducer apparatus 100 may also include a tunneler 104 is arranged and extends from the housing 102. The tunneler 104 may be configured to facilitate formation of the subcutaneous pocket for the medical device. In addition and as shown in FIG. 1, a portion 108 of the tunneler 104 may have a greater width than an end portion 110 of the tunneler 104. The portion 108, in certain instances, may have a width equal to or approximately equal to a width of the medical device. In addition, the portion 108 may have a width that is 1%, 5%, 10%, 15%, 20%, 25%, 30%, 35%, 40%, 45%, or 50% (or any percentage in between) greater than a width of the end portion 110. In addition, the end portion 110 may comprise a distal tip of the tunneler 104, which may facilitate movement of the tunneler 104 through the tissue of a patient. The end portion 110 may include a taper such that a depth or thickness of the end portion 110 decreases from the portion 108 toward the end portion 110 of the tunneler 104.

Figure 2A:
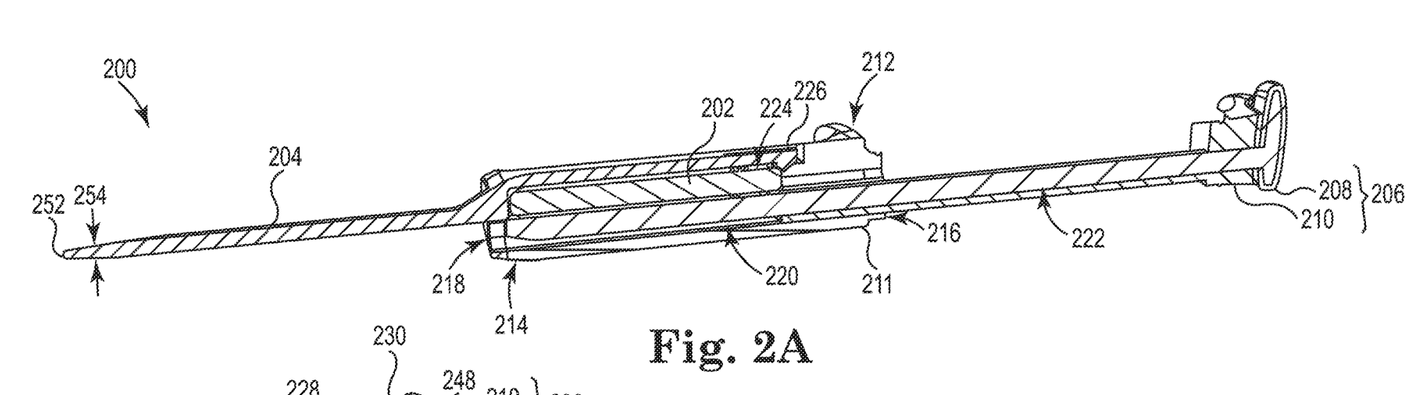
FIG. 2A is a cross-sectional perspective view of an illustrative introducer apparatus for a medical device, in accordance with embodiments of the disclosure.

FIG. 2A is a perspective view of an illustrative introducer apparatus 200 for a medical device 202, in accordance with embodiments of the disclosure. The introducer apparatus 200 includes a housing 211 having a proximal end 212 and a distal end 214. The housing may also define a proximal opening 216 at or adjacent to the proximal end 212 and a distal opening 218 at or adjacent to the distal end 214.

In certain instances, the introducer apparatus 200 may include a tunneler 204 extending from the distal end 214 of the housing 211. The tunneler 204 may be configured to facilitate forming a subcutaneous pocket for the medical device 202. In using the introducer apparatus 200, a user may first make an incision in a patient's skin. After the incision is made, the introducer apparatus 200 may be positioned within the incision. The medical device 202 may be positioned at a certain depth under the patient's skin. The tunneler 204 may facilitate pocket formation by tunneling the introducer apparatus 200 into the patient's tissue. More specifically, the tunneler 204 may include a distal tip 252 having a depth 254 that is less than a depth of remaining section of the tunneler 204. The depth 254 of the distal tip 252 may facilitate movement of tissue around the tunneler 204 in reaching the depth under the patient's skin.

The introducer apparatus 200 may also include an inserter 206. The inserter may be configured to form the subcutaneous pocket in the tissue and pass the medical device 202 through the distal opening 218 of the housing 211. As shown in FIG. 2A, the inserter 206 includes a first portion 208 and a second portion 210 of the inserter 206 that may be cooperatively used to form the subcutaneous pocket. The first portion 208 of the inserter 206 is configured to disengage from the second portion 210 of the inserter 206 to position the medical device within the subcutaneous pocket. In addition, the housing also may include a first channel 220 extending between the proximal opening 216 and the distal opening 218 along a length of the housing 211. Each of the first portion 208 of the inserter 206 and the second portion 210 of the inserter may be configured to move within the first channel 220 along the length of the housing.

The introducer apparatus 200 may also include a second channel 222. As noted above, the first portion 208 of the inserter 206 is configured to disengage from the second portion 210 of the inserter 206. The first portion 208 of the inserter 206 is also configured to move within the second channel 222. The second portion 210 of the inserter 206 surrounds the first portion 208 of the inserter 206 when the first portion 208 and the second portion 210 are engaged. In addition, the first portion 208 of the inserter 206 disengages from the second portion 210 of the inserter after the entirety of the first portion 208 of the inserter is moved, within the second channel 222, proximally relative to the housing 211. The second channel 222 may be an internal section of the second portion 210 of the inserter 206.

The housing 211 may also include a compartment 224 that is configured to releasably hold and contain the medical device 202. The compartment 224 may be offset relative to or laterally adjacent from the first channel 220. In addition, the compartment 224 may frictionally engage the medical device 202 to hold the medical device 202 within the compartment 224. In addition, the compartment 224 may include a snap-feature 226 that facilitates holding the medical device 202 within the compartment 224. The snap-feature 226 may be formed of a portion of the housing 211 that is moveable with respect to remaining portions of the housing 211. As a result, the snap-feature 226 may be configured to bend or tilt outwardly away from the compartment 224 and the first channel 220 by a user. The user may bend or tilt the snap-feature 226 away from the compartment 224 and the first channel 220 in order to load the medical device 202 in the compartment 224, and release the snap-feature 226 to secure the medical device 202 therein.

The medical device 202 may be released from the compartment 224 in response to the first portion 208 being moved proximally relative to the housing 211. Moving the first portion 208 of the inserter 206 proximally relative to the housing 211 may leave behind a space in the first channel 220, previously occupied by the first portion 208, and the medical device 202 may be released from the compartment 224 into the first channel 220. Subsequent movement of the first portion 208 and/or the second portion 210 of the inserter 206 distally relative to the housing 211 along the first channel 220 will also move the medical device 202 along the first channel 220. As a result, the medical device 202 may be deployed or ejected from the distal opening of 218 of the housing 211.

Figure 2B:
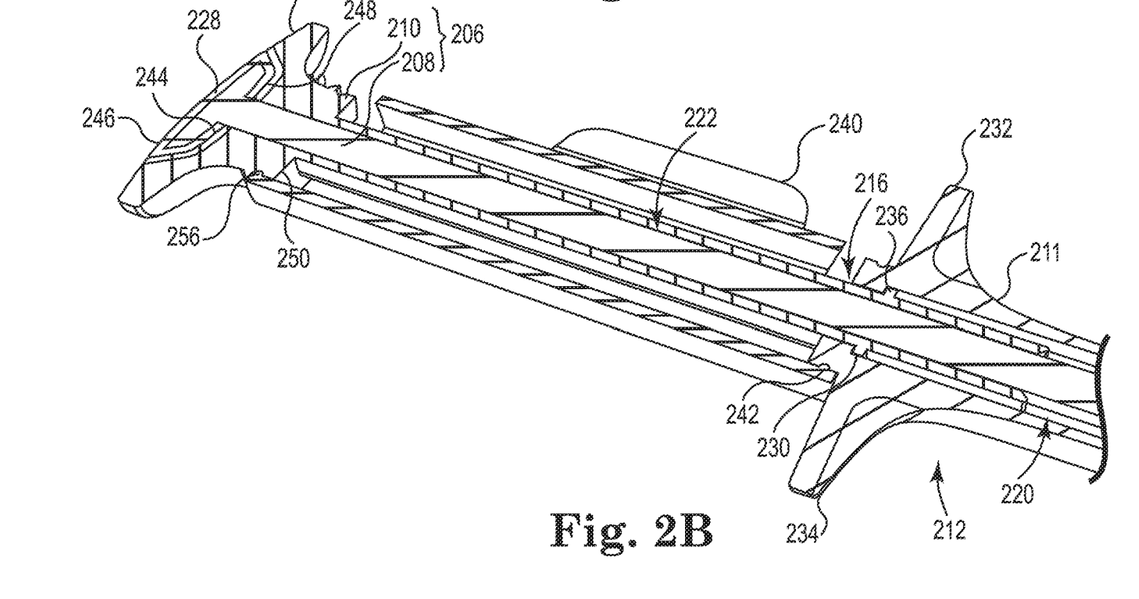
FIG. 2B is a cross-sectional perspective view of a proximal portion of a housing and an inserter of the illustrative introducer apparatus, as shown in FIG. 2B, in accordance with embodiments of the disclosure.

FIG. 2B is a cross-sectional perspective view of a proximal portion of the housing 211 and the inserter 206 of the illustrative introducer apparatus 200 as shown in FIG. 2B, in accordance with embodiments of the disclosure. As shown in FIG. 2B, the first portion 208 of the inserter 206 may include a first handle portion 228, and the second portion 210 of the inserter 206 may include a second handle portion 230. The handle portions 228, 230 provide a gripping surface for a user to, respectively, facilitate moving the first portion 208 and the second portion 210 of the inserter 206.

In certain instances, the handle portion 228 of the first portion 208 of the inserter 206 is configured to nest within the handle portion 230 of the second portion 210 of the inserter 206. More specifically and in certain instances, the first handle portion 228 may include a first lower surface 244 and a first upper surface 246. In addition, the second handle portion 230 may include a second upper surface 248 and a second lower surface 250. The first lower surface 244 and the second upper surface 248 are corresponding surfaces. The first lower surface 244 and the second upper surface 248 may take any shape so long as the first lower surface 244 and the second upper surface 248 mirror one another. For instance and as shown in FIG. 2B, the first lower surface 244 is convex, and the corresponding second upper surface 248 is concave.

Similar to the first portion 208 and the second portion 210 of the inserter 206, the housing 211 may also include handle portions 232, 234 arranged at the proximal end 212. The handle portions 232, 234 facilitate a user's ability to grip and move the housing 211 and the introducer apparatus 200.

As noted above, the first portion 208 of the inserter 206 is configured to disengage from the second portion 210 of the inserter 206. In certain instances, the second portion 210 of the inserter 206 may be coupled to the housing 211. Further, the second portion 210 of the inserter 206 may include lateral extensions 236, 238 that interface with the housing 211. The lateral extensions 236, 238 may prevent the second portion 210 of the inserter 206 from being separated or disengaged from the housing 211. More specifically, the lateral extensions 236, 238 have a greater width than a width of the proximal opening 216. In addition, the width of the lateral extensions 236, 238 may be sized to move along the first channel 220.

In certain instances, the introducer apparatus 200 may include a lock structure 240 that is removable from the housing 211. The lock structure 240 is configured to hold the first portion 208 and the second portion 210 of the inserter 206 relative to the housing 211 in an initial configuration. The lock structure 240 may also include a first protrusion 242 and/or a second protrusion 256 that interface with and frictionally engage a portion of the housing 211. As a result, the lock structure 240 is held in place until a user applies force to remove the lock structure 240 from the housing 211. In addition, each of the first portion 208 of the inserter 206 and the second portion 210 of the inserter 206 may be configured to move within the first channel 220 along the length of the housing after removal of the lock structure 240.

Figure 2C:
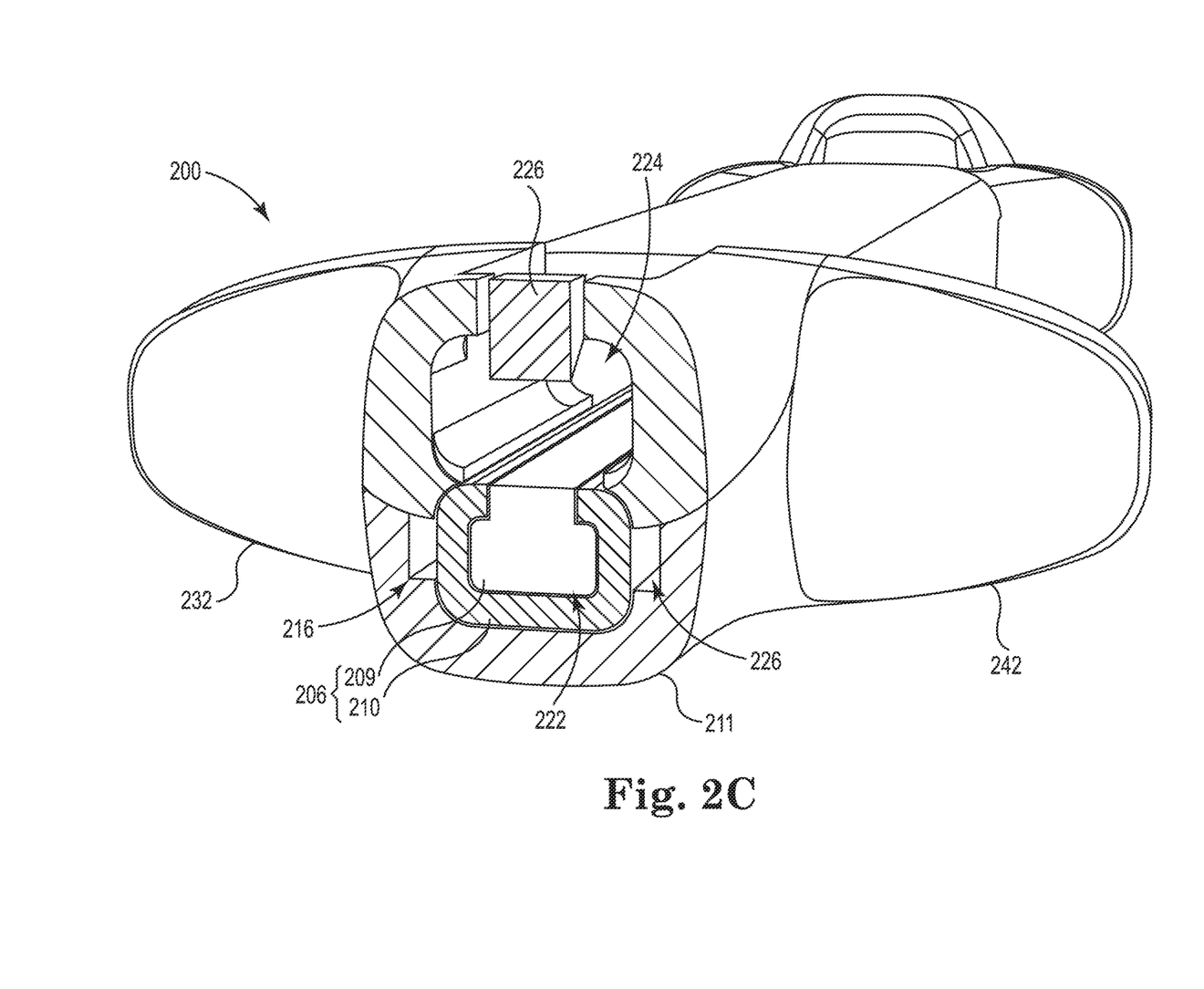
FIG. 2C is a cross-sectional perspective end view of the illustrative introducer apparatus, as shown in FIGS. 2A-B, in accordance with embodiments of the disclosure.

FIG. 2C is a cross-sectional perspective end view of the illustrative introducer apparatus 200, as shown in FIGS. 2A-B, in accordance with embodiments of the disclosure. As shown in FIG. 2C, the compartment 224 is laterally offset from the first channel 220. The snap-feature 226 is shown as a separate portion of the housing 211, which impinges the compartment 224 in an initial configuration (shown in FIG. 2C). As described above with reference to FIG. 2A, the snap-feature 226 may be configured to bend or tilt outwardly away from the compartment 224. The user may bend or tilt the snap-feature 226 away from the compartment 224 in order to load the medical device 202 (not shown in FIG. 2C) in the compartment 224, and release the snap-feature 226 to secure the medical device 202 therein. Release of the snap-feature 226 may make an audible sound (such as a click) as the result of the snap-feature 226 contacting the medical device 202 and/or the housing 211.

FIG. 2C also shows the first portion 208 and the second portion 210 of the inserter 206. As shown therein. The second portion 210 surrounds the first portion 208, and both the first portion 208 and the second portion 210 are contained within the first channel 220. As a result, a width of the first portion 208 may be smaller than a width of the second portion 210. The second channel 222 is occupied by the first portion 208 of the inserter in the configuration shown in FIG. 2C. As shown in FIG. 2C, the second portion 210 may include a "U" shape that is configured to form the second channel 222 and move/pass the first portion 208 of the inserter 206 therethrough.

Each of FIGS. 3A-G may be illustrative of steps in a method of subcutaneous implanting a medical device using an introducer apparatus. The illustrative components shown in FIGS. 3A-G are not intended to suggest any limitation as to the scope of use or functionality of embodiments of the disclosed subject matter. Neither should the illustrative components be interpreted as having any dependency or requirement related to any single component or combination of components illustrated therein. As a result, the illustrative introducer apparatus shown in FIGS. 3A-G, and the components associated therewith, may be, in embodiments, integrated with various other components depicted therein (and/or components not illustrated), all of which are considered to be within the ambit of the disclosed subject matter. For example, the illustrative introducer apparatuses depicted in FIG. 1 and FIG. 2A-C may be used as the introducer apparatus in a method of subcutaneous implanting a medical device.

Figure 3A:
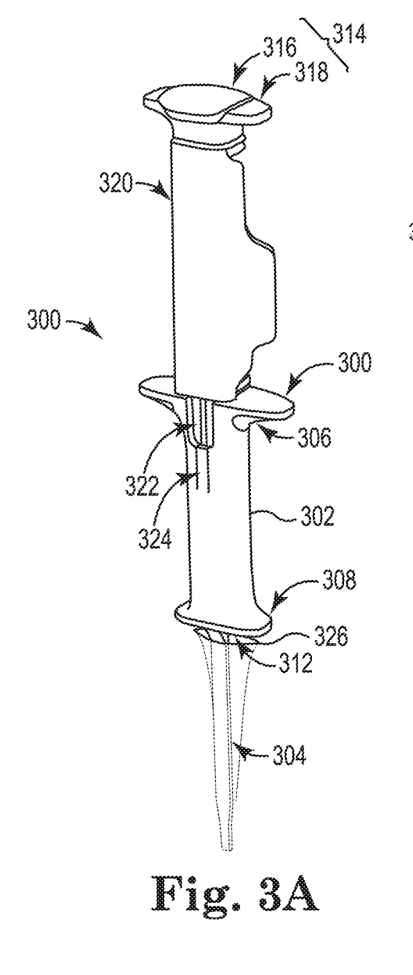
FIG. 3A is a perspective view of an illustrative introducer apparatus for a medical device including a removable lock structure, in accordance with embodiments of the disclosure.

FIG. 3A is a perspective view of an illustrative introducer apparatus 300 for a medical device (shown in FIGS. 3F-G) including a removable lock structure 320, in accordance with embodiments of the disclosure. The introducer apparatus 300 includes a housing 302. The housing 302 may include a compartment 322 that is configured to releasably hold the medical device. The compartment 322 may include a snap-feature 324 that facilitates holding the medical device within the compartment 322. The medical device may be loaded into the compartment 322 in this configuration. In certain instances, the medical device may also be loaded into the compartment 322 at any point prior to ejecting the device from the housing 302. In addition, the housing 302 has a proximal end 306 and a distal end 308. Further, the housing 302 may define a proximal opening 310 (shown in FIG. 3B) and a distal opening 312 (shown in FIGS. 3E-F). The housing 302, the compartment 322, and each of the proximal opening 310 and distal opening 312 may be formed or manufactured to accommodate medical devices of various sizes.

The introducer apparatus 300 may also include a tunneler 304 arranged at and extending from the distal end 308 of the housing 302. The tunneler 304 is configured to facilitate forming a subcutaneous pocket for the medical device. The introducer apparatus 300 may also include an inserter 314 configured to pass the medical device through the distal opening 312 of the housing 302. The inserter 314 may include a first portion 316 and a second portion 318 that are cooperatively used to form the subcutaneous pocket. As discussed in further detail below, the first portion 316 is configured to disengage from the second portion 318, and the second portion 318 to position the medical device within the subcutaneous pocket.

In certain instances, the introducer apparatus 300 may include a removable lock structure 320 configured to hold the first portion 316 and the second portion 318 relative to the housing 302 in an initial configuration (as shown in FIG. 3A). A user will remove the removable lock structure 320 from the housing 302 in order to move the first portion 316 and the second portion 318.

As shown in FIG. 3A, the introducer apparatus 300 is shown positioned within an incision 326. The tunneler 304 is also positioned within the incision 326. After the incision is made, the tunneler 304 may facilitate pocket formation by tunneling the introducer apparatus 300 into the patient's tissue through the incision. The medical device may be positioned at a certain depth under the patient's skin. As a result, the tunneler 304 facilitates movement of tissue around the tunneler 304 in reaching the depth under the patient's skin. In certain instances, the tunneler 304 is positioned within the incision 326 such that the distal opening 312 of the housing 302 abuts the incision 326.

Figure 3B:
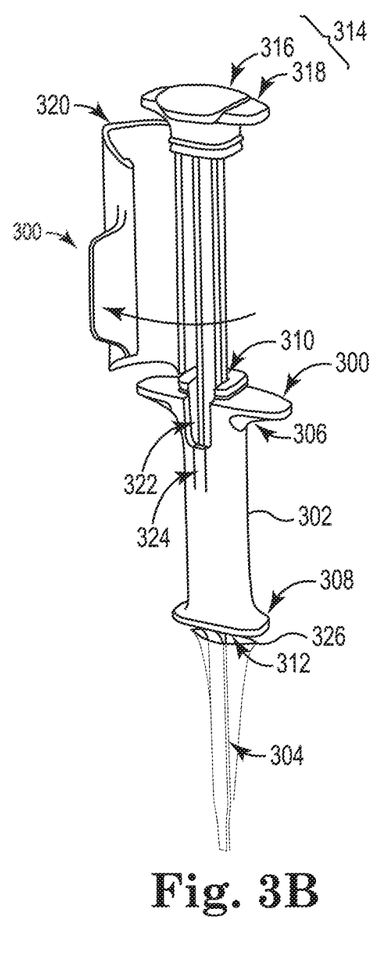
FIG. 3B is a perspective view of the illustrative introducer apparatus, as shown in FIG. 3A, with the removable lock structure removed from the introducer apparatus, in accordance with embodiments of the disclosure.

FIG. 3B is a perspective view of the illustrative introducer apparatus, as shown in FIG. 3A, with the removable lock structure 320 removed from the introducer apparatus 300, in accordance with embodiments of the disclosure. In order to move the removable lock structure 320, a user may twist or rotate the removable lock structure 320 relative to the housing 302 to disengage the removable lock structure 320. After the removable lock structure 320 is removed from the introducer apparatus 300, the inserter 314 may move relative to the housing 302.

Figure 3C:
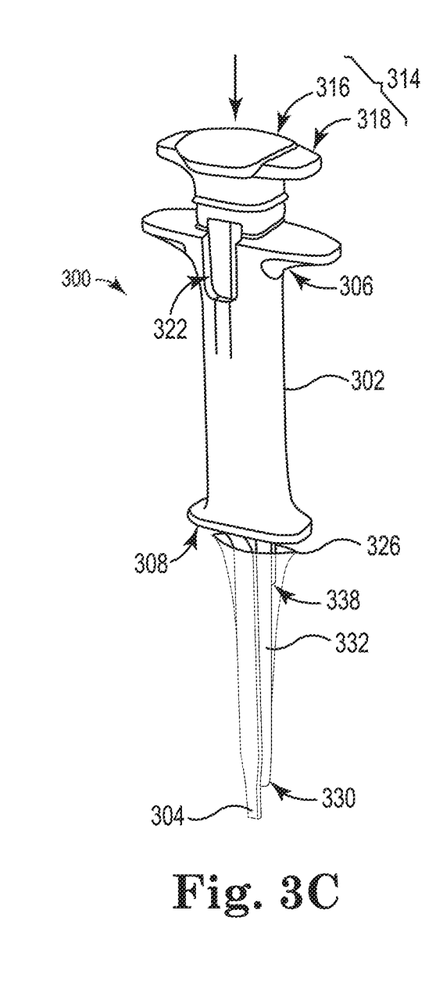
FIG. 3C is a perspective view of the illustrative introducer apparatus, as shown in FIGS. 3A-B, using the inserter to create a subcutaneous pocket, in accordance with embodiments of the disclosure.

FIG. 3C is a perspective view of the illustrative introducer apparatus 300, as shown in FIGS. 3A-B, using the inserter 314 to create a subcutaneous pocket, in accordance with embodiments of the disclosure. The inserter 314 is moved proximally relative to the housing 302 (from the configuration shown in FIG. 3B) to create the subcutaneous pocket. In certain instances, the first portion 316 is configured to create the subcutaneous pocket. The first portion 316 may include a proximal end 328 (shown in further detail in FIG. 3D) and a distal end 330. The first portion 316 also may include a first extension portion 332. As discussed in further detail below with reference to FIGS. 3E-F, the second portion 318 includes a second extension portion 340 (shown in FIG. 3E). Each of the first extension portion 332 and the second extension portion 340 (shown in FIG. 3E) are configured to extend through the distal opening 312 (shown in FIGS. 3E-F) of the housing 302 in a fully-extended configuration of the first portion 316 and the second portion 318. As shown in FIG. 3C, a distal end 330 of the first extension portion 332 extends through the housing 302, and a distal end 338 of the second extension portion (shown in FIGS. 3E-F) the distal opening 312.

In certain instances, extending the first portion 316 of the inserter 314 through the distal opening 312 of the housing 302 (and into the patient's skin) forms a subcutaneous pocket for the medical device. Forcing the first portion 316 of the inserter 314 through tissue beneath the incision 326 opens space thereby creating the pocket for implanting the medical device. In embodiments, the first portion 316 forces apart tissue under the patient's skin without rotation of the housing 302 or the inserter 314.

Figure 3D:
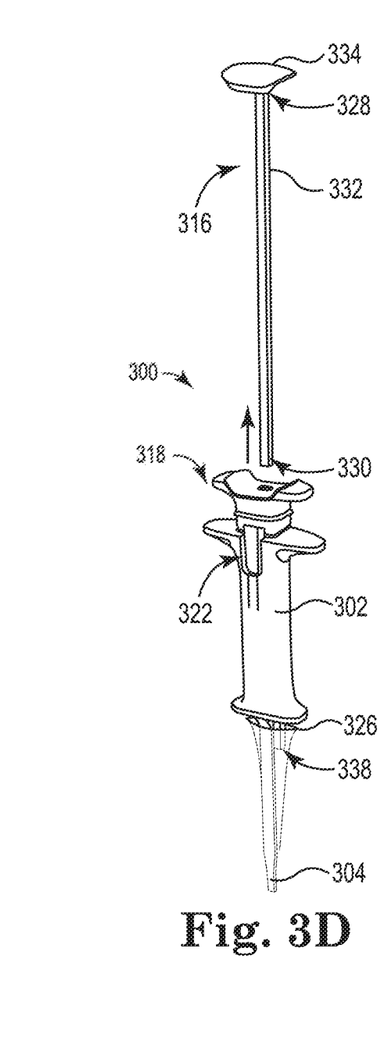
FIG. 3D is a perspective view of the illustrative introducer apparatus, as shown in FIGS. 3A-C, having a first portion of the inserter disengaged from a second portion of the inserter, in accordance with embodiments of the disclosure.

FIG. 3D is a perspective view of the illustrative introducer apparatus 300, as shown in FIGS. 3A-C, having the first portion 316 of the inserter 314 disengaged from the second portion 318 of the inserter 314, in accordance with embodiments of the disclosure. After the first portion 316 of the inserter 314 has created the pocket, the first portion 316 of the inserter 314 maybe withdrawn proximally relative to the housing 302. As shown in FIG. 3D, the first portion 316 of the inserter 314 is configured to disengage from the housing 302. The second portion 318 of the inserter 314 may remain extended through the housing 302 during removal of the first portion 316. The second portion 318 may hold the medical device 346 positioned within the subcutaneous pocket during removal of the first portion 316. As a result, the medical device 346 will not eject from the subcutaneous pocket due to the removal of the first portion 316 because the second portion 318 holds the medical device 346 in place. Thus, the first portion 316 and the second portion 318 may be configured to form the subcutaneous pocket without rotation of the housing or the inserter. As shown in FIG. 3D, the distal end 338 remains body within the incision 326.

Figure 3E:
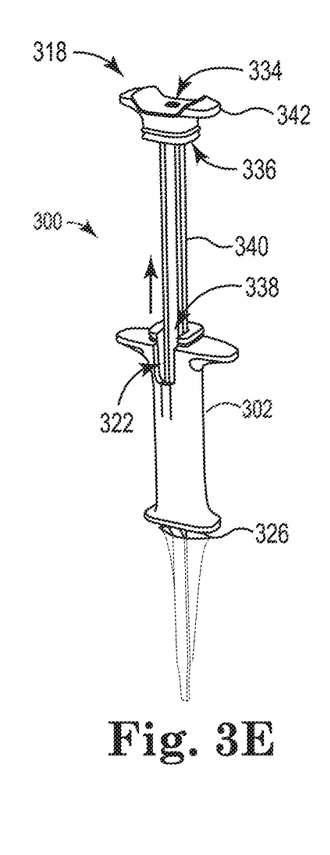
FIG. 3E is a perspective view of the illustrative introducer apparatus, as shown in FIGS. 3A-D, having the second portion of the inserter pulled back from the housing prior to moving the medical device into the pocket, in accordance with embodiments of the disclosure.

FIG. 3E is a perspective view of the illustrative introducer apparatus 300, as shown in FIGS. 3A-D, having the second portion 318 of the inserter pulled back from the housing 302 prior to moving the medical device into the pocket, in accordance with embodiments of the disclosure. After the first portion 316 of the inserter 314 has created the pocket and been disengaged from the second portion 318 of the inserter 314, the second portion 318 may be moved proximally relative to the housing 302. As described with reference to FIGS. 2A-B, moving the second portion 318 in this step may position the medical device for implantation. The medical device may release from the compartment 322 into the pathway of the second portion 318 of the inserter 314. The medical device is transitioned into a loading configuration by removing the first portion 316 of the inserter 314 and moving the second portion 318 proximally into a loading configuration (shown in FIG. 3E).

Structural differences between the first portion 316 and the second portion 318 may be seen in comparing FIG. 3D and FIG. 3E. For instance, the first portion 316 of the inserter 314 may include a proximal end 328 and the distal end 330, a first handle portion 334 arranged at the proximal end 328 of the first portion 316. The first extension portion 332 extends from the first handle portion 334. In addition, the second portion 318 may include a proximal end 336 and the distal end 338, and a second handle portion 342 arranged at the proximal end 336 of the second portion 318. The second portion 318 may also include a second extension portion 340 extending from the second handle portion 342. In addition, the second portion 318 may include a second channel 344 along a length of the second extension portion 340.

As shown in comparing FIG. 3D and FIG. 3E, the first extension portion 332 has a first length and the second extension portion 340 has a second length, with the first length being greater than the second length. The differences in length between the first extension portion 332 and the second extension portion 340 is also shown in FIG. 3C with the distal end 330 of the first extension portion 332 extending further into the patient than the distal end 338 of the second extension portion 340.

Figure 3F:
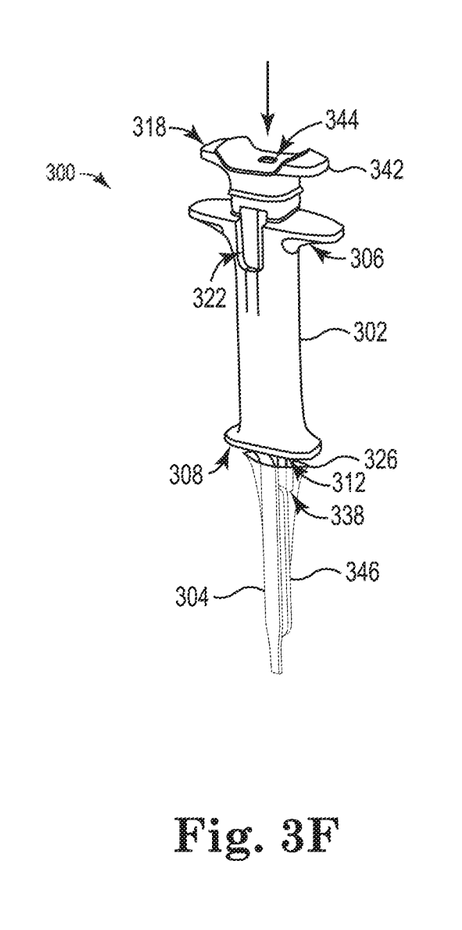
FIG. 3F is a perspective view of the illustrative introducer apparatus, as shown in FIGS. 3A-E, using the second portion of the inserter to insert the medical device in the pocket, in accordance with embodiments of the disclosure.
Figure 3G:
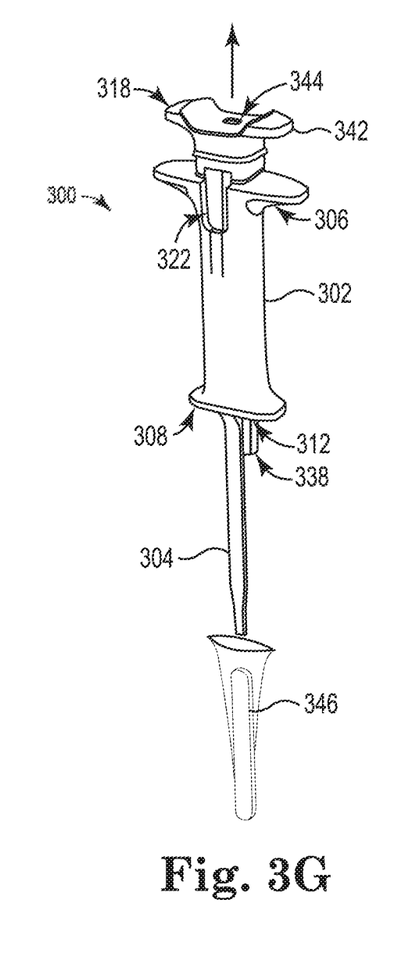
FIG. 3G is a perspective view of the illustrative introducer apparatus, as shown in FIGS. 3A-F, with the medical device implanted and the introducer apparatus removed from the pocket, in accordance with embodiments of the disclosure.

FIG. 3F is a perspective view of the illustrative introducer apparatus 300, as shown in FIGS. 3A-E, using the second portion 318 of the inserter 314 to insert the medical device 346 in the pocket, in accordance with embodiments of the disclosure. As shown in FIG. 3F, the second portion 318 of the inserter 314 is moved distally relative to the housing 302 to eject the medical device 346 through the distal opening 312 of the housing 302 via the second portion 318. The second portion 318 of the inserter 314 is shown in a fully-extended configuration with the first portion 316 being disengaged from the second portion 318. In addition, the second extension portion 340 may be configured to extend through the distal opening 312 of the housing 302 in the fully-extended configuration. As is shown in FIG. 3F, the distal end 338 of the second portion 318 extends through the housing 302 to eject the medical device 346 therefrom. FIG. 3G is a perspective view of the illustrative introducer apparatus 300, as shown in FIGS. 3A-F, with the medical device 346 implanted and the introducer apparatus 300 removed from the pocket, in accordance with embodiments of the disclosure.

The illustrative components shown in FIGS. 3A-G are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in FIGS. 3A-G may be, in embodiments, integrated with various other components depicted therein (and/or components not illustrated), all of which are considered to be within the ambit of the disclosed subject matter. For example, first portion 316 may include a first channel extending between the proximal opening 310 and the distal opening 312 along a length of the housing 302 (e.g., as discussed above with reference to FIGS. 2A-C).

In certain instances, any of the illustrative introducer apparatuses described herein and an implantable medical device may be provided as a system. In addition to the introducer apparatus and the implantable medical device, the system may also include a device for making an incision in a patient. This device for making the incision (not shown) may be any device having a sharp edge (such as scalpel). In addition, the incision may be made using a plunge cutter, or, for example, a vibratory plunge cutter as discussed in U.S. Provisional Patent No. 62/159,510, Titled "Vibratory Plunge Cutter," and herein incorporated by reference.

Various modifications and additions can be made to the illustrative embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. An introducer system for facilitating subcutaneous implantation of a medical device, the system comprising:
 a medical device;
 a housing having a proximal end and a distal end, a distal opening at or near the distal end;
 a tunneler extending from the distal end of the housing and configured to form a subcutaneous pocket for the medical device, wherein the tunneler is not hollow;
 an inserter configured to move along a pathway to pass the medical device through the distal opening of the housing;
 a compartment arranged within the housing and configured to releasably hold and contain the medical device prior to the inserter moving the medical device; and
 a snap-feature integrally formed by the housing such that the snap-feature is moveable with respect to remaining portions of the housing and arranged such that the snap-feature facilitates holding the medical device within the compartment before ejection.

2. The system of claim 1, wherein the compartment is configured to frictionally engage the medical device and release the medical device into the pathway of the inserter.

3. The system of claim 2, wherein the compartment is configured to release the medical device into the pathway of the inserter in response to withdrawal of the inserter toward the proximal end of the housing.

4. The system of claim 3, wherein the compartment is laterally adjacent the pathway of the inserter.

5. The system of claim 1, wherein the snap-feature is configured to bend or tilt outwardly relative to the compartment to secure the medical device therein.

6. The system of claim 5, wherein the snap-feature is configured to feedback to a user that the medical device is secured within the compartment.

7. An introducer system for facilitating subcutaneous implantation of a medical device, the system comprising:
   a medical device;
   a housing having a proximal end and a distal end, a distal opening at or near the distal end;
   a tunneler extending from the distal end of the housing and configured to form a subcutaneous pocket for the medical device, wherein the tunneler is tapered such that a depth or thickness of the tunneler decreases toward an end portion of the tunneler, wherein the tunneler is not hollow;
   a compartment arranged within the housing configured to frictionally engage and hold the medical device prior to the subcutaneous implantation;
   an inserter configured to allow release of the medical device into a pathway of the inserter in response to withdrawal of the inserter toward the proximal end of the housing and move the medical device along the pathway through the distal opening of the housing for the subcutaneous implantation.

8. The system of claim 7, wherein the compartment is laterally adjacent the pathway of the inserter.

9. The system of claim 7, wherein the compartment is laterally adjacent the distal opening of the housing.

10. The system of claim 7, wherein the compartment includes a snap-feature integrally formed by the housing such that the snap-feature is moveable with respect to remaining portions of the housing.

11. The system of claim 7, wherein the tunneler extends from the distal end of the housing with at least a portion of the tunneler being in a common plane with the compartment.

12. The system of claim 7, wherein the compartment includes a feature integrally formed of a portion of the housing that is moveable with respect to remaining portions of the housing to facilitate engagement with the medical device.

13. The system of claim 7, wherein the inserter is arranged to obstruct the medical device from being arranged within the pathway in a partially withdrawn configuration.

14. The system of claim 7, wherein the compartment and the pathway are of substantially similar widths.

15. A method of subcutaneous implanting a medical device using an introducer apparatus comprising a housing having a proximal end, a distal end, and a distal opening defined by the housing, and a tunneler extending from the housing, an inserter, a compartment arranged within the housing configured to releasably hold and contain the medical device, and a snap-feature integrally formed by the housing such that the snap-feature is moveable with respect to remaining portions of the housing; the method comprising:
   making an incision in a patient's skin;
   positioning the introducer apparatus within the incision using the tunneler to facilitate formation of a subcutaneous pocket, wherein the tunneler is not hollow;
   withdrawing the inserter toward the proximal end of the housing to move the medical device into a pathway of the inserter;
   temporarily holding the medical device in the compartment by contacting the medical device with the snap-feature; and
   moving the inserter toward the distal end of the housing to move the medical device along the pathway, out of the distal opening, and into the subcutaneous pocket.

16. The method of claim 15, wherein moving the inserter toward the distal end of the housing facilitates movement of the medical device from the compartment laterally adjacent the pathway of the inserter into the pathway of the inserter.

17. The method of claim 15, wherein the inserter is arranged to obstruct the medical device from being arranged within the pathway prior to moving the inserter toward the distal end of the housing.

18. The method of claim 15, wherein the compartment and the pathway are of substantially similar widths.

\* \* \* \* \*